United States Patent [19]

Bosman

[11] Patent Number: 4,848,364

[45] Date of Patent: Jul. 18, 1989

[54] COVERING SHEET WHICH CAN BE MADE FORM-RETAINING

[75] Inventor: Cornelis R. Bosman, Wassenaar, Netherlands

[73] Assignee: Patentico Ltd., Jersey, Channel Islands

[21] Appl. No.: 112,726

[22] Filed: Oct. 23, 1987

[30] Foreign Application Priority Data

Oct. 23, 1986 [NL] Netherlands .......................... 8602662

[51] Int. Cl.⁴ ............................................ A61F 13/00
[52] U.S. Cl. .................................... 128/849; 128/850; 128/87 R
[58] Field of Search .............. 128/82, 83, 87 R, 89 R, 128/DIG. 20, 132 R, 132 D, 155, 156, 849, 850; 446/369; 297/DIG. 1; 5/456

[56] References Cited

U.S. PATENT DOCUMENTS

| | | | |
|---|---|---|---|
| 3,212,497 | 10/1965 | Dickinson | 128/DIG. 20 X |
| 3,244,169 | 4/1966 | Baxter | 128/82 |
| 3,745,998 | 7/1973 | Rose | 128/87 R X |
| 3,762,404 | 10/1973 | Sakita | 128/DIG. 20 X |
| 3,972,332 | 8/1976 | Wakim | 128/303 R |
| 4,508,112 | 4/1985 | Seeler | 128/89 R |
| 4,533,352 | 8/1985 | Van Beek et al. | 604/317 |
| 4,657,003 | 4/1987 | Wirtz | 128/133 |

FOREIGN PATENT DOCUMENTS

| | | | |
|---|---|---|---|
| 7101392 | 8/1922 | Netherlands. | |
| 661204 | 7/1987 | Switzerland | 128/132 R |

Primary Examiner—Robert A. Hafer
Assistant Examiner—Kevin G. Rooney
Attorney, Agent, or Firm—Michael N. Meller

[57] ABSTRACT

Covering sheet, which can be made form-retaining particularly for surgical use, with an airtight cover to be placed under vacuum, flexible opposite outer walls enclosing two layers of flexible fiber material enclosing granular particles fixed in place.

3 Claims, 1 Drawing Sheet

U.S. Patent        Jul. 18, 1989        4,848,364
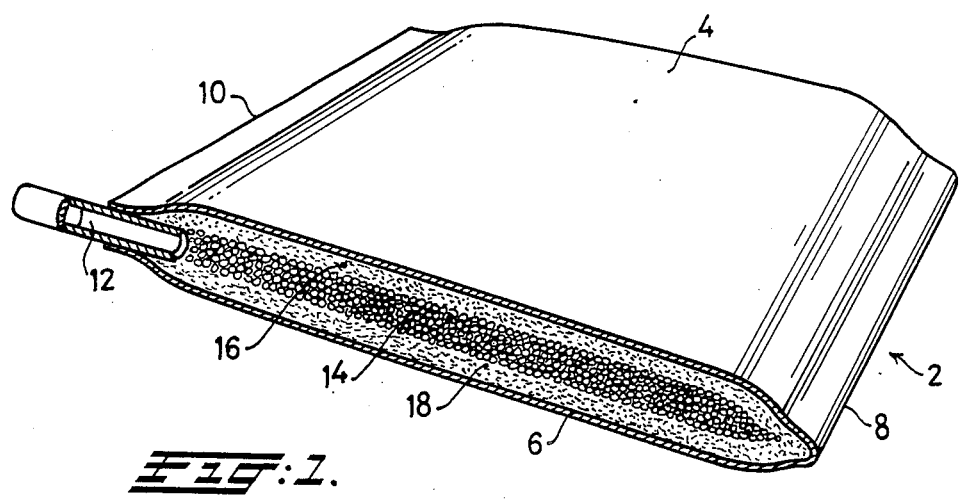

COVERING SHEET WHICH CAN BE MADE FORM-RETAINING

BACKGROUND OF THE INVENTION

The invention relates to a covering sheet which can be made form-retaining.

Such a covering sheet has many uses, for example for the temporary masking of objects when the surroundings thereof have to undergo a surface treatment, but a special application is the use during a surgical operation for covering certain organs which are not involved in the operation. Hitherto for this purpose compresses have been used but they have the disadvantage that they do not stay in place during the operation: they slip away and constantly have to be returned to the correct place. The same disadvantage applies to other known coverings.

SUMMARY OF THE INVENTION

The object of the invention is to eliminate this disadvantage and to provide a covering sheet which, when placed around the object or organ to be covered and following the contours thereof can be made formretaining, and thus remains in place. This object is achieved by the provision of an airtight covering which can be placed under vacuum, having two flexible opposite outside walls, and two layers of flexible fibre material therebetween, the space between these layers of fibre material containing granular or ball-shaped particles, fixed in place.

In a preferred embodiment the particles are fixed to at least one of the layers of flexible fibre material.

In another embodiment a number of the particles are combined, by means of the interconnecting flexible longitudinal and cross bars lying in one plane and formed integrally therewith, to a flat matrix, at least two of which are accommodated in the covering.

Through the shaping for fitting and placing under vacuum of the covering, the covering will deform three-dimensionally to a rigid whole which retains the shape obtained for fitting, and will thus no longer be able to shift relative to the object of organ.

DESCRIPTION OF THE DRAWINGS

FIG. 1 is a partially cut-away, perspective drawing of a first embodiment according to the invention.

FIG. 2 is a partial cross section of a second embodiment.

FIG. 3 shows the fitting of the covering sheet according to the invention round an organ prior to vacuum suction.

FIG. 4 shows the same situation as that according to FIG. 3, but after vacuum suction.

DESCRIPTION OF PREFERRED EMBODIMENTS

The embodiment of the covering sheet according to the invention shown in FIG. 1, indicated in its entirety by reference number 2, is made up of two flexible films 4, 6 which form the external walls, and which are connected to each other in sealing fashion along the four edges such as the edges 8 and 10 shown in the figure. Disposed at a suitable point, for example halfway along one of the edges or at a corner, is a connection 12 for a vacuum line, in such a way that it is airtight with the casing thus formed.

Inside the casing thus formed is a layer of granules 14 made of expanded foam between two thin layers 16, 18 of non-woven fabric. The distribution must be such or at least part of the granules is fastened to the layers of non-woven fabric in such a way that the granules cannot accumulate at one side of the covering. This is possible, for example, by covering the layers of non-woven fabric with a thin layer of adhesive and then sprinkling the granules over it. The total thickness of the layer of granules 14 can be, for example, three times the diameter of the granule.

FIG. 2 shows a partial cross section through another embodiment according to the invention, in which loose granules are replaced by flat matrices made up of balls connected to each other by thin bars. Such matrices can be produced by injection moulding. FIG. 2 shows the flexible external films 20, 22 and the non-woven fabic layers 24, 26; disposed between them are the three matrices 30, 32, 34, each consisting of balls 36, which are connected by means of thin longitudinal bars 38 and thin cross bars 40, in such a way that each ball is always confined between two longitudinal connections 38 and cross connections 40, with the exception of those which are situated along the edges of the matrix.

FIG. 3 shows how the covering sheet 2—which is shown partially cut away—can be folded around the organ 50 to be covered and in the process moulds fully to all contours thereof. After vacuum suction through the connection 12, the situation shown in FIG. 4 arises; the covering sheet has become a rigid entity, the layer of granules 14 has, as it were, "hardened", and through the complete moulding of the covering sheet 2 to the contours of the organ 50, the covering sheet no longer needs to be held in place by additional means.

What is claimed is:

1. A covering sheet which can be shaped to conform to the shape of an object to be covered, comprising:
    a flexible casing comprising first and second walls connected at their perimeters and defining a chamber which is sealed except for an opening;
    exhaust outlet means coupled to said opening and adapted to allow the covering sheet to be placed under a vacuum to retain the shape of the covered object;
    first and second layers of flexible fiber material attached respectively to the inner sides of said first and second walls and having a space formed therebetween;
    a plurality of particles filling said space between said first and second layers of flexible fiber material, at least some of said particles being attached to at least one of said layers of flexible fiber material.

2. The covering sheet according to claim 1, wherein said particles are expanding foam granules, and further comprising a thin layer of adhesive covering said at least one of said layers of flexible fiber material, said at least some of said granules being adhered to said at least one of said layers of flexible fiber material by said thin layer of adhesive.

3. The covering sheet according to claim 1, wherein said particles are balls, further comprising means for interconnecting said balls into first and second arrays, said first array overlying said second array, said interconnecting means comprising a plurality of flexible bars, each flexible bar interconnecting two balls and each ball being interconnected to at least two other balls.

* * * * *